United States Patent [19]

Iijima et al.

[11] Patent Number: 4,824,833
[45] Date of Patent: Apr. 25, 1989

[54] BENZOXAZINE DERIVATIVES

[75] Inventors: Ikuo Iijima, Urawa; Masakatsu Ozeki, Wako; Kunihito Okumura, Urawa; Masanori Inamasu, Misato, all of Japan

[73] Assignee: Tanabe Seiyaku Co., Ltd., Japan

[21] Appl. No.: 167,344

[22] Filed: Mar. 14, 1988

[30] Foreign Application Priority Data

Mar. 18, 1987 [JP] Japan .................................. 62-65360

[51] Int. Cl.$^4$ .................... A61K 31/535; C07D 413/10
[52] U.S. Cl. .................................. 514/230.5; 544/105
[58] Field of Search .............. 544/105; 514/231, 230.5

[56] References Cited

U.S. PATENT DOCUMENTS 4,619,687 10/1986 Haga et al. ................................. 71/92
4,729,784  3/1988 Kume et al. ............................ 71/95
4,734,124  3/1988 Chang et al. ............................ 71/92

Primary Examiner—Richard L. Raymond
Attorney, Agent, or Firm—Scully, Scott, Murphy & Presser

[57] ABSTRACT

Novel benzoxazine derivative of the formula:

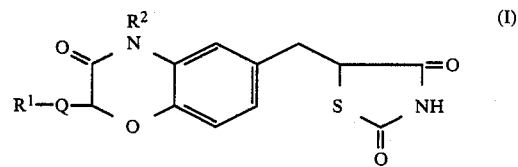

wherein $R^1$ is phenyl group or a substituted thiazolyl group; $R^2$ is hydrogen atom or a lower alkyl group; Q is single bond or a lower alkylene group, or a salt thereof are disclosed. Said derivative (I) and a salt thereof are useful as therapeutic agents for diabetes.

7 Claims, No Drawings

BENZOXAZINE DERIVATIVES

This invention relates to a novel benzoxazine derivative and processes for preparing same. More particularly, it relates to a benzoxazine derivative of the formula:

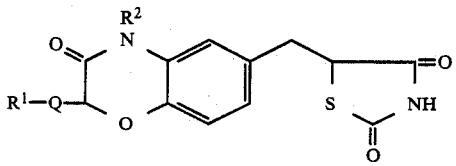
(I)

wherein $R^1$ is phenyl group or a substituted thiazolyl group; $R^2$ is hydrogen atom or a lower alkyl group; and Q is single bond or a lower alkylene group, or a salt thereof.

A variety of biguanide derivatives and sulfonylurea derivatives have been so far used for treatment of diabetes. However, these anti-diabetic agents are still unsatisfactory in that the biguanide and sulfonylurea derivatives cause side effects such as lactic acidosis and severe hypoglycemia, respectively.

The novel benzoxazine derivative (I) of the present invention and a salt thereof are useful for therapeutic treatment of diabetes because they elevate insulin sensitivity in cells and show potent hypoglycemic activity.

Examples of the benzoxazine derivative of the present invention include those of the formula (I) in which $R^1$ is phenyl group or a phenyl-thiazolyl group; $R^2$ is hydrogen atom or a lower alkyl group; and Q is single bond or a lower alkylene group.

Among them, the preferred subgenus includes the benzoxazine derivative (I) in which $R^1$ is phenyl group or 2-phenyl-thiazol-4-yl group; $R^2$ is hydrogen atom or methyl group; and Q is single bond or methylene group, or a salt thereof.

The present invention includes within its scope the benzoxazine derivative (I) in which lower alkyl groups and lower alkylene groups are alkyl groups and alkylene groups of 1 to 6 carbon atoms; but the compounds (I) in which alkyl groups and alkylene groups of 1 to 4 carbon atoms are usually exemplified as preferred examples of those.

The benzoxazine derivative (I) of the present invention may exist in the form of four isomers due to two asymmetric carbon atoms thereof. The present invention includes within its scope either one of these isomers and a mixture thereof.

According to the present invention, the compound (I) or a salt thereof can be prepared by the step or steps of:

(1) hydrolyzing an imine compound of the formula:

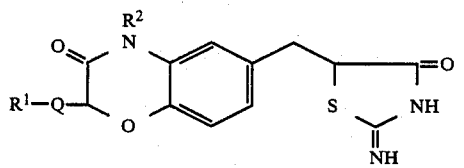
(II)

wherein the symbols are the same as defined above, or a salt thereof, or (2) reducing an olefin compound of the formula:

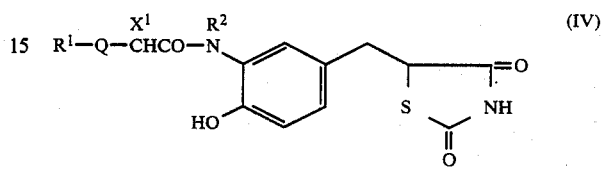
(III)

wherein the symbols are the same as defined above, or a salt thereof, or (3) subjecting a halide compound of the formula:

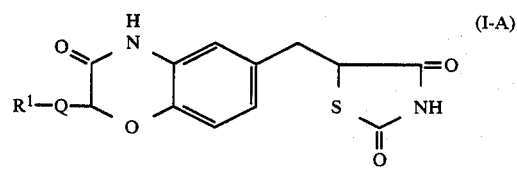
(IV)

wherein $X^1$ is a halogen atom and the other symbols are the same as defined above, or a salt thereof, to intramolecular cyclization, and (4) if required, converting the product to a salt thereof.

The compound (I) in which $R^2$ is a lower alkyl group, or a salt thereof, may also be prepared by alkylation of the compound of the formula:

(I-A)

wherein the symbols are the same as defined above, or a salt thereof, and if required, converting the product into a salt thereof.

The compound (I-A) and the starting compounds (II) to (IV) may, if required, be used for the above reactions in the form of an acid addition salt (e.g., hydrochloride), an alkali metal salt or an alkaline earth metal salt.

The hydrolysis of the imino compound (II) or a salt thereof can be conducted in a conventional manner. For example, it can be carried out by treating the compound (II) with an acid such as hydrochloric acid, hydrobromic acid, trifluoroacetic acid or methanesulfonic acid in an inert solvent. It is preferred to carry out the reaction between 50° and 150° C.

The reduction of the olefin compound (III) or a salt thereof can be conducted in the presence of a catalyst in an inert solvent. Examples of the catalyst include palladium-carbon, palladium, platinum oxide, Raney nickel and the like. It is preferred to carry out the reaction in hydrogen atomsphere between 10° and 80° C.

The intramolecular cyclization of the halide compound (IV) or a salt thereof can be conducted in the presence of an acid acceptor in an inert solvent. Examples of the acid acceptor include an alkali metal bicarbonate, an alkali metal carbonate, an organic base such as an alkali metal acetate, triethylamine, N,N-dimethylaniline or pyridine, and the like. It is preferred to carry out the reaction between 0° and 100° C.

The alkylation of the compound (I-A) or a salt thereof can be conducted by treating it with an alkylating agent in the present of an acid acceptor in an inert solvent. Examples of the alkylating agent include lower alkyl halides (e.g., methyl iodide, ethyl bromide and the like), and an alkali metal hydroxide, an alkali metal carbonate, an alkali metal hydride, an alkali metal lower alkoxide and the like are preferably used as the acid acceptor. It is preferred to carry out the reaction between 0° and 100° C.

In carrying out either one of the above-mentioned reactions, conventional solvents such as ethanol, methanol, tetrahydrofuran, dioxane and the like may be used.

The benzoxazine derivative (I) of the present invention and a salt thereof exhibit potent hypoglycemic activity and are useful for treatment and/or prophylaxis of diabetes, especially for the treatment of patients with non-insulin dependent diabetes. For example, the effect of 2-(2-phenylthiazol-4-yl)methyl-6-[(2,4-dioxothiazolidin-5-yl)methyl]-3-oxo-1,4,benzoxazine on blood glucose level in KK—A$^y$ mise (Tokyo Laboratory Animals Science Corp., Tokyo, Japan) fed powdered chow (CE2, Clea Japan Inc., Tokyo, Japan) containing 5 mg% of the test compound for 5 days was tested. In this experiment, when blood was collected from the tail tip and glucose was enzymatically measured, the average blood glucose level in the medicated group was about 60% lower than that in the non-medicated group. Such therapeutic effect of the compound (I) is based on elevation of insulin sensitivity in cells and, unlike the known anti-diabetic agents, said compound is advantageous in that it can be used as anti-diabetic agent without affecting patients of normal blood glucose level. Moreover, the toxicity of the benzoxazine derivative (I) of the present invention is low. For example, when 2-(2-phenylthiazol-4-yl)methyl-6-[(2,4-dioxothiazolidin-5-yl)-methyl]-3-oxo-1,4,benzoxazine at a dose of 100 mg/kg (CMC suspension) was orally administered to mice, no mice died during a 72 hour-observation period.

The benzoxazine derivative (I) can be used for pharmaceutical use either in the free form or in the form of a salt. Suitable salts of the compound (I) for pharmaceutical use include, for example, pharmaceutically acceptable salts such as an alkali metal salt (e.g., sodium salt, potassium salt), an alkaline earth metal salt (e.g., calcium salt, magnesium salt), and acid addition salts (hydrochloride or sulfate). Such salt may be obtained by treating the compound (I) with a stoichiometrically equimoler amount of the acid or base according to a conventional manner.

The compound (I) and a salt thereof may be administered either orally or parenterally and may also be used in the form of a pharmaceutical preparation containing the same compound in admixture with pharmaceutical excipients suitable for oral or parenteral administration. The pharmaceutical preparations may be in solid form such as tablets, capsules or suppositories or in liquid form such as solutions, suspensions or emulsions. Moreover, when administered parenterally, the pharmaceutical preparation may be used in the form of injections.

The dose of the compound (I) or a salt thereof may vary depending on the age, condition and body weight of patients, the kind and severity of diseases to be treated and administration route, etc, but may usually be about 0.05 to about 100 mg/kg, preferably about 0.1 to about 50 mg/kg, per day.

All of the starting compounds of the present invention are novel. Among them, the starting compound (II) may be prepared, for example, by diazotizing a compound of the formula:

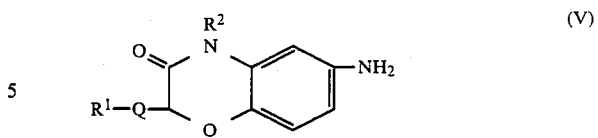

wherein the symbols are the same as defined above, in the presence of a hydrogen halide, reacting the diazotized product with methyl acrylate in the presence of a copper catalyst (e.g., copper (I) oxide) to give a compound of the formula:

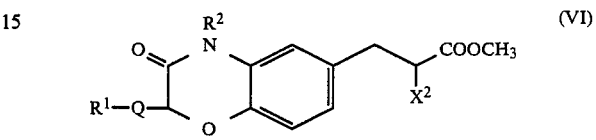

wherein $X^2$ is a halogen atom and the other symbols are the same as defined above, and then reacting the compound (VI) with thiourea in the presence of a base such as sodium acetate.

The starting compound (III) may be prepared, for example, by condensing a compound of the formula:

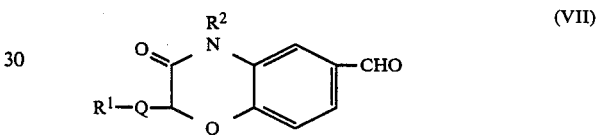

wherein the symbols are the same as defined above, with 2,4-dioxothiazolidine in the presence of a base such as piperidine, or subjecting a compound of the formula:

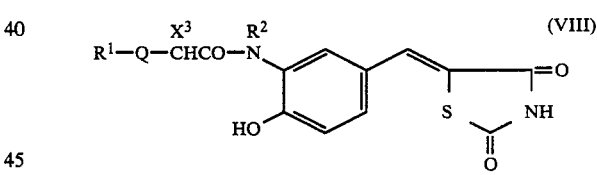

wherein $X^3$ is a halogen atom and the other symbols are same as defined above, to intramolecular cyclization in the the same manner as in the case of the halide compound (IV).

The starting compound (IV) may be prepared, for example, by condensing a compound of the formula:

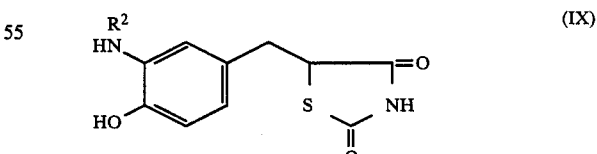

wherein the symbols are the same as defined above, with a compound of the formula:

wherein the symbols are the same as defined above, in a conventional manner.

The starting compounds (II) to (IV) thus prepared and the compound (I-A) may be used in the reactions of the invention, if desired, without isolation and purification.

EXAMPLE 1

(1) A solution of 1.3 g of sodium nitrite in 3 ml of water is added to a mixture of 4.8 g of 6-amino-2-benzyl-3-oxo-1,4-benzoxazine, 3 ml of conc. hydrochloric acid and 60 ml of acetone. After the mixture is stirred at room temperature for 30 minutes, 10.6 ml of methyl acrylate are added thereto, and 500 mg of copper oxide (I) are added gradually at a temperature of 35° to 40° C. After stirring for 30 minutes, the mixture is poured into water and extracted with ethyl acetate. The extract is washed, dried and evaporated to remove the solvent. The residue is purified by silica gel column chromatography (solvent; chloroform:methanol=100:1) to give 4.95 g of crude methyl 3-(2-benzyl-3-oxo-1,4-benzoxazin-6-yl)-2-chloropropionate.

Yield 73%.

m.p. 124°–127° C.

IR$\nu_{max}^{Nujol}$(cm$^{-1}$): 1750, 1700, 1610.

Mass(m/e): 361, 359(M$^{30}$), 323.

(2) A solution of 4.9 g of the product obtained above, 2.07 g of thiourea and 1.3 g of sodium acetate in 30 ml of ethylene glycol monomethyl ether is heated at 100° C. for 7 hours. After cooling, the reaction mixture is poured into water. Crystalline precipitates are collected by filtration, washed with water and ether and dried to give 3.78 g of 2-benzyl-6-[(2-imino-4-oxothiazolidin-5-yl)methyl]-3-oxo-1,4-benzoxazine.

Yield 76%.

m.p. 251°–254° C. (dec.).

IR$\nu_{max}^{Nujol}$(cm$^{-1}$): 1680, 1640.

Mass(m/e): 367(M+), 252.

(3) A mixture of 3.78 g of the product obtained above, 2.86 g of p-toluenesulfonic acid monohydrate, 6 ml of water and 30 ml of ethylene glycol monomethyl ether are heated for 4 hours. Then, the reaction mixture is poured into water, and extracted with ethyl acetate. The extract is washed with a saturated aqueous sodium chloride solution, dried and evaporated to remove the solvent. The residue is purified by silica gel column chromatography (solvent; chloroform:methanol=10:1) to give 3.2 g of 2-benzyl-6-[(2,4-dioxothiazolidin-5-yl)methyl]-3-oxo-1,4-benzoxazine as pale brown foam.

Yield 84%.

IR$\nu_{max}^{Nujol}$(cm$^{-1}$): 1750, 1690.

Mass(m/e): 368(M+), 253, 252.

EXAMPLES 2 TO 4

(1) The corresponding starting compounds are treated in the same manner as described in Example 1-(1) to give the compounds shown in Table 1.

TABLE 1

Structure (V) → (VI) where $X^2 = Cl$

| Ex. No. | $R^1-Q-$ | $R^2$ | Properties |
|---|---|---|---|
| 2 | phenyl | H | Yield 72%<br>M.p. 121–124° C.<br>IR*: 1750, 1690 |
| 3 | phenyl | CH$_3$ | Yield 69%<br>oil<br>IR*: 1750, 1680 |
| 4 | benzyl | CH$_3$ | Yield 81%<br>oil<br>IR*: 1745, 1685 |

IR* = IR$\nu_{max}^{Nujol}$(cm$^{-1}$):
("IR*" means the same in the following lines.)

(2) The products obtained above are treated in the same manner as described in Example 1-(2) to give the compounds shown in Table 2.

TABLE 2

Structure (VI) → (II) where $X^2 = Cl$

| Ex. No. | $R^1-Q-$ | $R^2$ | Properties |
|---|---|---|---|
| 2 | phenyl | H | Yield 55%<br>M.p. 268–271° C. (dec.)<br>IR*: 1690, 1640, 1600 |
| 3 | phenyl | CH$_3$ | Yield 98%<br>M.p. 205–208° C.<br>IR*: 1670, 1600 |

TABLE 2-continued

[Structure VI: R¹—Q—O—CH(R²N-C(=O))—...—C₆H₄—CH₂—CH(X²)—COOCH₃]

(VI)

↓

[Structure II: similar with thiazoline ring, X² = Cl]

(II)

| Ex. No. | Compound (II) R¹—Q— | R² | Properties |
|---|---|---|---|
| 4 | [benzyl] | CH₃ | Yield 72% M.p. 141–144° C. IR*: 1670, 1535 |

(3) The products obtained above are treated in the same manner as described in Example 1-(3) to give the compounds shown in Table 3.

TABLE 3

[Structure II] →

[Structure I]

| Ex. No. | Compound (I) R¹—Q— | R² | Properties |
|---|---|---|---|
| 2 | [phenyl] | H | Yield 76% M.p. 219–222° C. IR*: 1760, 1740, 1700 |
| 3 | [phenyl] | CH₃ | Yield 65% M.p. 193–195° C. IR*: 1740, 1680 |
| 4 | [benzyl] | CH₃ | Yield 76% M.p. 198–203° C. IR*: 1750, 1700 |

EXAMPLES 5 TO 8

The corresponding starting compounds are treated in the same manner as described in Example 1-(1) to (3) to give the compounds shown in Table 4.

TABLE 4

[Structure V: with NH₂ group] →

[Structure I]

| Ex. No. | Compound (I) R¹—Q— | R² | Properties |
|---|---|---|---|
| 5 | [2-phenylthiazol-5-yl] | H | Yield 55% M.p. 247–250° C. IR*: 1750, 1690 |
| 6 | [2-phenylthiazol-5-yl] | CH₃ | Yield 62% IR*: 1750, 1690 |
| 7 | [2-phenyl-4-ethylthiazol-5-yl] | H | Yield 54% IR*: 1750, 1690 |
| 8 | [2-phenyl-4-ethylthiazol-5-yl] | CH₃ | Yield 67% IR*: 1750, 1690 |

[Preparation of the starting compounds]

Preparation 1

(1) A mixture of 12.0 g of 3-phenylpropionic acid, 25 ml of thionylchloride and 8 ml of carbon tetrachloride are heated at 70° C. for 45 minutes. Then, 10.7 g of N-bromosuccinimide, 40 ml of carbon tetrachloride and 6 drops of 48% hydrobromic acid are further added thereto, and the mixture is heated for 1 hour. After cooling, insoluble materials are filtered off, and the filtrate is condensed to dryness. The residue is dissolved in 20 ml of tetrahydrofuran, and the mixture is added dropwise to 120 ml of a tetrahydrofuran solution containing 12.3 g of 2-amino-4-nitrophenol and 14.5 g of N,N-dimethylaniline under ice cooling. After stirring at room temperature for 40 minutes, the mixture is evaporated to remove the solvent. Water is added to the residue, and the mixture is extracted with ethyl acetate, dried and evaporated to remove the solvent. Then, the residue is dissolved in 200 ml of acetone. 41.4 g of potassium carbonate are added thereto, and the mixture is refluxed for 1 hour. After cooling, the reaction mixture is poured into water. Crystalline precipitates are collected by filtration, washed with water, dried and recrystallised from a mixture of ethyl acetate and n-hexane to give 12.25 g of 2-benzyl-6-nitro-3-oxo-1,4-benzoxazine.

Yield 54%.

m.p. 194.5°–197.5° C.

IR$\nu_{max}^{Nujol}$(cm$^{-1}$): 1685, 1520, 1340.

Mass(m/e): 284(M+).

(2) A mixture of 6.5 g of the product obtained above, 5.0 g of methyl iodide, 10.0 g of potassium carbonate and 50 ml of dimethylformamide is stirred at room temperature for 1 hour. The reaction mixture is poured into water. Crystalline precipitates are collected by filtration, washed with water and dried to give 5.86 g of 2-benzyl-4-methyl-6-nitro-3-oxo-1,4-benzoxazine.

Yield 86%.

m.p. 166°–169° C.

IR$\nu_{max}^{Nujol}$(cm$^{-1}$): 1695, 1520.

Mass(m/e): 298(M+).

(3) 6.2 g of the product obtained above are dissolved in a mixture of 100 ml of methanol and 100 ml of tetrahydrofuran, and the mixture is subjected to catalytic reduction in the presence of 3.0 g of 10% palladium-carbon. After the reaction, the catalyst is filtered off, and the filtrate is condensed to dryness to give 6-amino-2-benzyl-4-methyl-3-oxo-1,4-benzoxazine.

Yield 91.5%.

m.p. 82°–85° C.

IR$\nu_{max}^{Nujol}$(cm$^{-1}$): 3430, 3340, 1680, 1610.

Preparation 2 to 8

The corresponding starting compounds are treated in the same manner as described in Preparation 1 to give the compounds shown in Table 5. [In Preparation 2, 4, 5 & 7 the starting compounds are treated in the same manner as described in Preparation 1-(1) & (3), and in Preparation 3, 6 & 8 in the same manner as described in Preparation 1-(1) to (3)]

TABLE 5

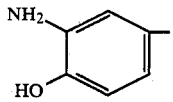

| Pr. No. | Compound (V) R$^1$—Q— | R$^2$ | Properties |
|---|---|---|---|
| 2 | 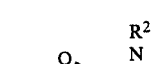 | H | M.p. 195–198° C. (dec.) IR*: 3470, 3380, 1690, 1640 |
| 3 |  | CH$_3$ | M.p. 165–168° C. IR*: 3460, 3360, 1680, 1620 |
| 4 |  | H | M.p. 186–189° C. (dec.) IR*: 3420, 3340, 1680, 1630 |
| 5 |  | H | M.p. >210° C. (dec.) IR*: 3470, 3380, 1690 |
| 6 |  | CH$_3$ | IR*: 3350, 1670, 1610 |
| 7 |  | H | M.p. 195–197° C. IR*: 3430, 3340, 3210, 1680, 1520 |

TABLE 5-continued

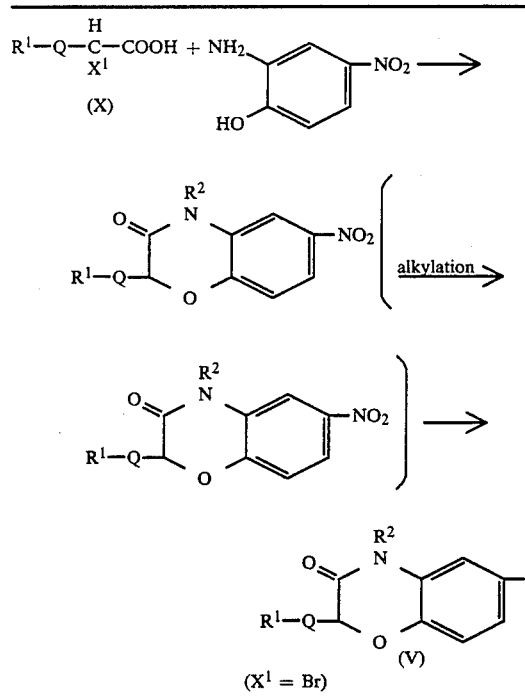

What is claimed is:
1. A benzoxazine derivative of the formula:

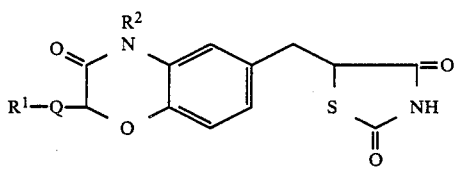

wherein $R^1$ is a phenyl group or a phenyl-thiazolyl group; $R^2$ is an hydrogen atom or a lower alkyl group; Q is a single bond or a lower alkylene group, or a pharmaceutically acceptable salt thereof.

2. The compound claimed in claim 1, in which $R^2$ is hydrogen atom or a $C_{1-4}$ alkyl group; and Q is single bond or a $C_{1-4}$ alkylene group, or a pharmaceutically acceptable salt thereof.

3. The compound claimed in claim 2, in which $R^1$ is phenyl group or 2-phenyl-thiazol-4-yl group; $R^2$ is hydrogen atom or methyl group; and Q is single bond or methylene group, or a pharmaceutically acceptable salt thereof.

4. 2-[(2-phenylthiazol-4-yl)methyl]-6-[(2,4-dioxothiazolidin-5-yl)methyl]-3-oxo-1,4-benzoxazine, or a pharmaceutically acceptable salt thereof.

5. 2-(2-phenylthiazol-4-yl)-6-[(2,4-dioxothiazolidin-5-yl)methyl]-3-oxo-1,4-benzoxazine, or a pharmaceutically acceptable salt thereof.

6. A pharmaceutical composition which comprises a pharmaceutically effective amount of the compound claimed in any one of claims 1 or 2-5 and a pharmaceutically acceptable carrier thereof.

7. A method for treatment or prophylaxis of a diabetes in a warm-blood animal which comprises administering to said warm-blood animal a pharmaceutically effective amount of the compound claimed in any one of claims 1, or 2-5.

* * * * *

UNITED STATES PATENT AND TRADEMARK OFFICE
CERTIFICATE OF CORRECTION

PATENT NO. : 4,824,833

DATED : April 25, 1989

INVENTOR(S) : Ikuo Iijima, et al.

It is certified that error appears in the above-identified patent and that said Letters Patent is hereby corrected as shown below:

Column 5, line 30: "$(M^{30})$" should read as --$(M^{+})$--

Column 9, line 66: "3,6 & 8" should read as --3, 6 & 8--

Signed and Sealed this

Twelfth Day of June, 1990

Attest:

HARRY F. MANBECK, JR.

Attesting Officer     Commissioner of Patents and Trademarks